Dec. 23, 1975
C. P. HARRIS
PLUM TREE
Filed Dec. 9, 1974
Plant Pat. 3,823
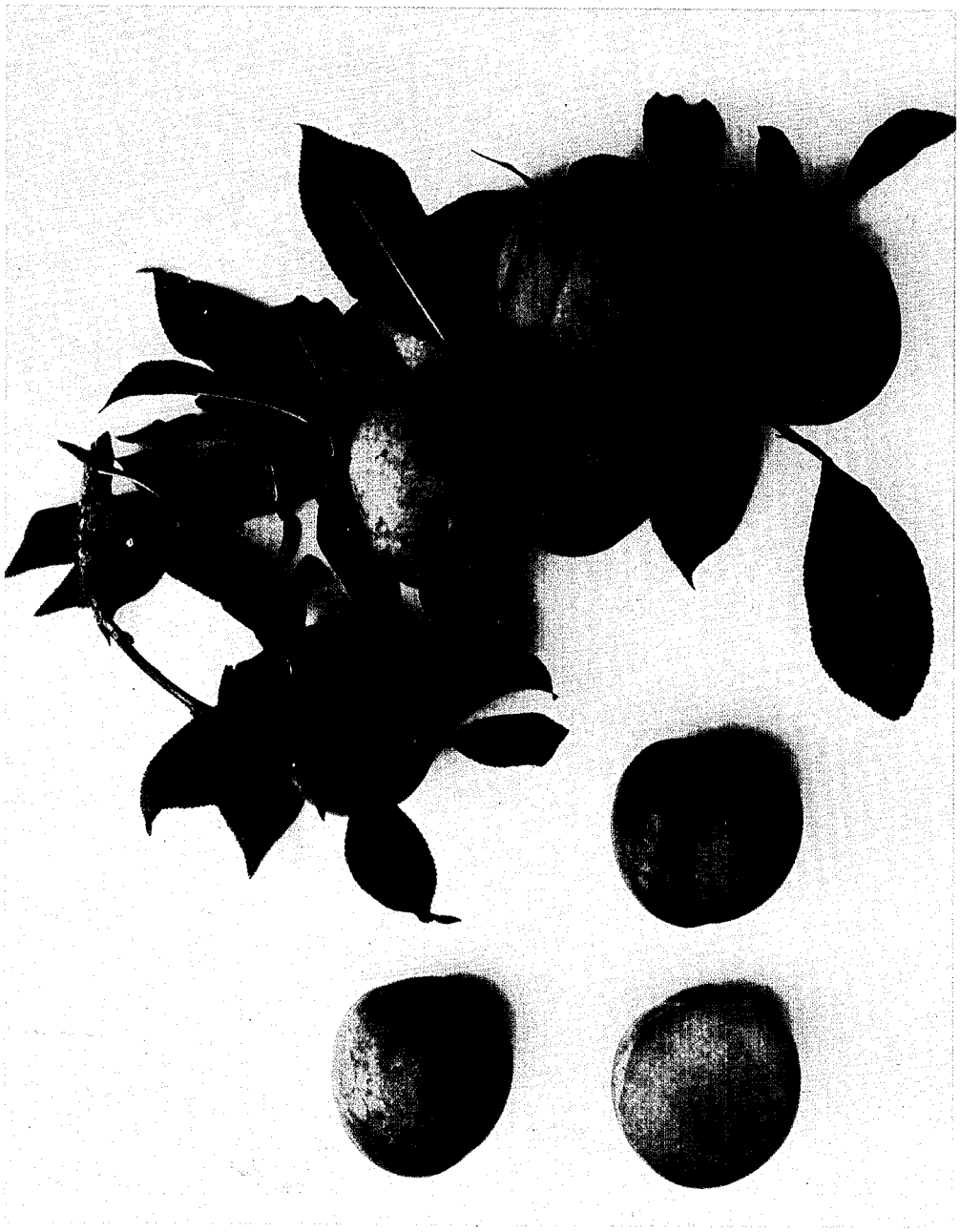

United States Patent

Plant Pat. 3,823

Patented Dec. 23, 1975

3,823

PLUM TREE

Caroline Payne Harris, Bakersfield, Calif., assignor to Plumwood Associates, Bakersfield, Calif.

Filed Dec. 9, 1974, Ser. No. 531,091

Int. Cl. A01h 5/03

U.S. Cl. Plt.—38 1 Claim

ABSTRACT OF THE DISCLOSURE

A plum tree which is vigorous, spreading, dense, round-topped, hardy, freely suckering, foliated with oblanceolate leaves having an acuminate tip, blooming early with white, uniform flowers borne in small custers on evenly dispersed spurs, and a productive bearer of large, substantially globose, clingstone fruit having purple skin with a silver-grey bloom, and deep red flesh.

ORIGIN OF THE VARIETY

The present variety of plum tree originated, in the yard of my residence in Bakersfield, Kern County, Calif., apparently as a fortuitous seedling. Curious as to the kind of tree the seedling would produce, I permitted it to grow—and continued to carefully observe it—after discovering its presence in my yard. In maturity, the tree—then recognized as a plum tree—bore fruit having characteristics which appeared novel, and I then undertook asexual reproduction of the tree in order to ascertain its potential for commercial growing.

ASEXUAL REPRODUCTION OF THE VARIETY

As the original tree was freely suckering, asexual reproduction was first accomplished by me, in the yard of my residence located as aforesaid, by severing and replanting rooted suckers or shoots which emerged from the root system of such original tree. Subsequently, the variety was further asexually reproduced, on my behalf, by a commercial nursery, by bud scions propagated on peach seedings in such nursery. In both instances, the reproductions ran true to the original tree in all respects, and were healthy, vigorous, and productive.

SUMMARY OF THE VARIETY

The present variety of plum tree is vigorous, spreading, dense, round-topped, hardy, freely suckering, foliated with oblanceolate leaves having an acuminate tip, blooming early with white, uniform flowers borne in small clusters on evenly dispersed spurs, and a productive bearer of large, substantially globose, clingstone fruit having purple skin with a silver-grey bloom, and deep red flesh; the tree being characterized, in addition to its profuse suckering and ease of asexual reproduction from rooted suckers and hardwood cuttings, by bearing fruit—of excellent quality—having a general exterior appearance similar to the Santa Rosa (unpatented), but ripening a few days later and having distinctive deep red flesh.

By further comparison, the fruit and the flesh, of the present variety, bear general resemblance to the Mariposa (Plant Patent No. 111), while the skin, bloom, and pit are more similar to the Elephant Heart (unpatented).

BRIEF DESCRIPTION OF THE DRAWING

The drawing is an illustration, by photographic reproduction in color, of a twig with leaves and fruit, and separate fruit, one of the latter being partially cut away to expose the flesh.

DESCRIPTION OF THE VARIETY

The botanical details of this new distinct variety of plum tree—with color definitions (except those in common color terms) referenced to Maerz and Paul Dictionary of Color—are as follows:

TREE:
- *Vigor.*—Moderate to vigorous.
- *Growth.*—Spreading.
- *Density.*—Dense.
- *Form.*—Round-topped. Tree readily adapts to open-vase tree-training system.
- *Hardiness.*—Hardy.
- *Production.*—Productive.

TRUNK:
- *Size.*—Medium to stocky.
- *Texture.*—Shaggy. External bark finely and evenly checked.
- *Color.*—Slate to dull brown.

BRANCHES:
- *Size.*—Medium to stocky.
- *Color.*—Slate to dull brown.
- *Texture.*—Bark evenly checked and noticeably thicker than Santa Rosa.
- *Lenticels:* Number—Medium. Size—Uniform.

LEAVES:
- *Size.*—Medium to large. Average length—4". Average width—1⅞".
- *Form.*—Oblanceolate. Acuminate tip.
- *Texture.*—Medium.
- *Color.*—Top side—Medium to deep green (23–L–10). *Gloss:* Medium to dull; under side—lighter green (22–K–7).
- *Veins.*—Distinct. Light green.
- *Margin.*—Finely and unevenly crenate.
- *Glands.*—Only on the petiole end at leaf.
- *Leaf Glands.*—Small. Non-uniform. Attached to basal end of leaf.
- *Stipules.*—None.

FLOWER BUDS:
- *Size.*—At full bud stage—¼" to 5/16" in diameter.

FLOWERS:
- *Blooming Period.*—Early, as compared with other varieties.
- *Stem.*—Medium to thin. Average length—9/16".
- *Petals.* — Evenly grouped. 5 count. Flat. Average length—⅜". Average width—5/16". White. Obtuse.
- *Pistil and Anthers.*—Equal in length.
- *Form.*—Uniform when fully open.
- *Aroma.*—Distinct. Sweet. Attractive to bees.
- *Flower Dispersion.*—Uniform.
- Flower Clusters.—Small. Usually 2 or 3 on evenly dispersed spurs.

FRUIT:
- *Maturity When Described.* — Fully matured, firm ripe.
- *Date of First Picking.*—June 20th.
- *Date of Last Picking.*—July 4th.
- *Size.*—Large. Average diameter axially—2¼". Average transversely in suture plane—2¼".
- *Form.*—Nearly perfectly round; i.e., substantially globose.
- *Suture.*—Smooth. Well filled from base to apex.
- *Ventral Surface.*—Smooth.
- *Cavity.*—Small. Distinctly deep.
- *Base.*—Broad. Uniform. Firm.
- *Apex.*—Round. Without point or depression.
- *Apex Marking.*—A distinct widening at the suture surface is present on the very apex of all fruit; such surface being dull yellow and smooth. No fruit cracking evident at apex of fruit.

SKIN:

*Thickness.*—Medium to thin.
*Texture.*—Smooth.
*Tenacity.*—Tenacious to flesh.
*Color.*—Purple red (55–L–12) shading darker to deep purple (56–E–11).
*Bloom.*—Moderate to light. Easily removed. Silver-grey (38–E–2).

FLESH:

*Color.*—Red (7–L–4). *Surface of Pit Cavity:* Deep-maroon.
*Amygdalin.*—Moderate.
*Juice.*—Moderate. Mellow. Sweet.
*Texture.*—Medium firm.
*Fibers.*—Few. Fine. Tender.
*Ripens.*—Evenly.
*Flavor.*—Mellow. Sweet. Sub-acid. Distinct.
*Aroma.*—Pronounced.
*Eating Quality.*—Excellent.

STONE:

*Type.*—Cling. Flesh adheres to all surfaces of the stone.
*Fibers.*—Very short.
*Size.* — Small. Average length — 15/16". Average width—11/16". Average thickness—3/8".
*Form.*—Oblong. Similar to Elephant Heart and Satsuma (unpatented).
*Base.*—Evenly tapered to hilum.
*Hilum.*—Small. Narrow. Oblong.
*Apex.*—Acuminate to rounded. Very small point.
*Sides.*—Uniform.
*Surface.*—Roughly pitted on both surfaces.
*Ridges.*—Pronounced. Rough. Sharp.
*Ventral Edge.*—Thin. Rough.

*Dorsal Edge.*—Deep groove. Rough.
*Pits.*—Well developed.
*Color.*—Beige (12–I–7).

USE: Dessert.—Market—local and long distance shipping.
KEEPING QUALITY: Good.
SHIPPING QUALITY: Good.
RESISTANCE TO DISEASES AND INSECTS: Equal to other commercial varieties.

The tree and its fruit herein described may vary in slight detail due to climatic and soil conditions under which the variety may be grown; the present description being of the variety as grown in the Central Valley of California.

I claim:

1. A new and distinct variety of plum tree, substantially as illustrated and described, which is vigorous, spreading, dense, round-topped, hardy, freely-suckering, foliated with oblanceolate leaves having an acuminate tip, blooming early with white, uniform flowers borne in small clusters on evenly dispersed spurs, and a productive bearer of large, substantially globose, clingstone fruit having purple skin with a silver-grey bloom, and deep red flesh; the tree being characterized, in addition to its profuse suckering and ease of asexual reproduction from rooted suckers and hardwood cuttings, by bearing fruit—of excellent quality—having a general exterior appearance similar to the Santa Rosa, but ripening a few days later and having distinctive deep red flesh.

No references cited.

ROBERT E. BAGWILL, Primary Examiner